United States Patent
Humphrey et al.

(10) Patent No.: US 9,216,002 B2
(45) Date of Patent: Dec. 22, 2015

(54) PATIENT SUPPORT

(75) Inventors: Malcolm George Humphrey, Horsham (GB); Peter Doherty, Turners Hill (GB)

(73) Assignee: Elekta AB (Publ), Stockholm (SE)

( * ) Notice: Subject to any disclaimer, the term of this patent is extended or adjusted under 35 U.S.C. 154(b) by 952 days.

(21) Appl. No.: 13/420,881

(22) Filed: Mar. 15, 2012

(65) Prior Publication Data

US 2013/0239329 A1 Sep. 19, 2013

(51) Int. Cl.

| | | |
|---|---|---|
| *A61G 7/018* | (2006.01) | |
| *A61G 13/02* | (2006.01) | |
| *A61B 6/04* | (2006.01) | |
| *A61B 6/00* | (2006.01) | |
| *A61N 5/10* | (2006.01) | |
| *A61G 13/10* | (2006.01) | |

(52) U.S. Cl.
CPC ... *A61B 6/04* (2013.01); *A61B 6/56* (2013.01); *A61G 7/018* (2013.01); *A61G 13/02* (2013.01); *A61G 13/107* (2013.01); *A61N 5/1049* (2013.01); *A61N 2005/1074* (2013.01)

(58) Field of Classification Search
CPC ..... A61G 13/02; A61G 7/018; A61G 13/107; A61B 6/04; A61B 6/56; A61N 2005/1074
USPC .............. 5/616; 318/106, 107, 441, 442
See application file for complete search history.

(56) References Cited

U.S. PATENT DOCUMENTS

| 4,423,364 | A * | 12/1983 | Kompelien et al. .......... 318/440 |
|---|---|---|---|
| 5,279,011 | A * | 1/1994 | Schnelle .......................... 5/616 |
| 7,331,426 | B2 * | 2/2008 | Jahkonen ..................... 187/290 |
| 8,471,403 | B2 * | 6/2013 | Kahkipuro et al. ............ 307/46 |
| 9,075,102 | B2 * | 7/2015 | Ham |
| 2008/0016620 | A1 * | 1/2008 | Haras ............................... 5/601 |
| 2008/0088266 | A1 * | 4/2008 | Lucas et al. .................. 318/441 |
| 2008/0186027 | A1 * | 8/2008 | Kassai ......................... 324/318 |

OTHER PUBLICATIONS

16 Volt Small Modules—General Purpose Modules, http://www.maxwell.com/products/ultracapacitors/product.aspx?PID=16V-SMALL-MODULES, dated Mar. 15, 2012.
Maxwell Ultracapacitor Uninterruptible Power Supply (UPS) Solutions, http://www.maxwell.com/products/ultracapacitors/industries/industry.aspx?sid=UPS-SYSTEMS, dated Mar. 15, 2012.

* cited by examiner

*Primary Examiner* — Michael Trettel
(74) *Attorney, Agent, or Firm* — Sunstein Kann Murphy & Timbers LLP

(57) ABSTRACT

Standby power supplies for patient tables need frequent replacement of the lead-acid batteries on which they depend. We propose to feed the emergency power direct to the drive motors, subsequent to the control circuitry. This will reduce the load on the standby power system, allowing greater design freedom to select longer-lasting or less expensive energy stores.

8 Claims, 2 Drawing Sheets

PATIENT SUPPORT

FIELD OF THE INVENTION

The present invention relates to a patient support.

BACKGROUND ART

Patient supports are used in the medical field to support and (more importantly) position a patient relative to an item of medical equipment such as a radiotherapy device. The patient can lie in a prone or supine position on the support, which then lifts and moves the patient into the desired position relative to the item of medical equipment.

In the example of a radiotherapy device, this has an "isocentre" to and around which the therapeutic radiation is delivered. The device can be called upon to treat a lesion which may be in any of a range of positions within the patient, and thus the patient needs to be moved so as to place the lesion substantially at the isocentre. In addition, a radiotherapy device has an associated geometry by which the radiation is delivered, and the patient may have to be oriented relative to the device so as to take account of that geometry. For example, a gantry-arm linear accelerator radiotherapy device delivers radiation to the isocentre from a radiation head that rotates around the isocentre, thus meaning that the beam of radiation arrives from a range of directions within a vertical plane that includes the isocentre. It may be preferable or necessary to orient the patient so that sensitive organs are placed outside that plane, in order to minimise their dose. It will also be necessary to ensure that the rotation arc of the gantry is kept clear of obstructions.

The treatment position is therefore dictated by the medical apparatus and by the required prescription. It may bear little or no resemblance to a position that is accessible for the patient to get onto (or be placed onto) the support. Modern patient support systems therefore have the ability to adjust the patient position in all six degrees of freedom, both so that it can be moved from an accessible position to a treatment position, and also to allow adjustment of the treatment position as required. This requires a number of electrically-powered motors, and their associated control circuitry.

The control circuitry may be complex, and may be integrated with the control circuitry for the medical equipment so that the patient position can be controlled during treatment. Some items of medical equipment (such as, again, radiotherapy apparatus) include feedback systems that monitor the current location of a lesion within the patient and call for adjustments to the patient position so as to correct any positioning errors that are detected.

This presents a problem in the event of a power failure during treatment, in that the patient may be left in an inaccessible location, i.e. one from which they are unable (or unwilling) to dismount from the support, or one from which they cannot be lifted off by medical staff. This means that a backup power source must be provided; this is typically in the form of an uninterruptible power supply ("UPS"). These consist of a lead-acid battery together with control and sensing circuitry. When the primary power source is online, the lead-acid battery is charged. When the sensing circuitry detects a power loss, the lead-acid battery powers an inverter to provide AC power to replace the primary power source.

A result of this arrangement is that the battery is partially discharged each time the system is powered down, and then recharged again when the system is powered up. This repeated cycling of the battery means that it needs to be replaced every 12 months or so, to ensure it is always capable of holding enough charge to perform its function. As the backup battery has to power the entire table and the associated control system when the power fails, it is required to have a fairly large capacity. The consequence is that the running costs of the system are increased by having regularly to replace a substantial battery.

In recent times, so-called "ultracapacitors" have been proposed as alternatives to lead-acid batteries in UPS devices. However, their high cost and (relatively) lower capacities mean that their uses are largely confined to providing brief power in order to shut down IT equipment safely, or to "ride through" the period between the loss of a permanent primary power source and the arrival on-line of a secondary backup power source such as a local generator.

SUMMARY OF THE INVENTION

The current position regarding UPS arrangements is unsatisfactory. Lead-add accumulators require replacement too often at too high a cost. An ultracapacitor-based UPS is not suitable for use as a replacement, as the large capacity needed to power the patient support and its associated machine control system for long enough to allow the support to be lowered to a position where the patient can would call for a very expensive ultracapacitor. This would, in turn, negate the cost savings arising from not having regularly to replace the lead-add battery.

The present invention seeks to resolve these by providing a UPS-like device that takes power from mains AC in but delivers power back in to a point downstream of the control circuitry. This reduces the load on the UPS energy source (be it lead-acid or capacitive) and allows greater choice of cheaper or longer-lasting sources.

The present invention therefore provides a patient support, comprising a patient table provided with a control panel, at least one electrically-powered motor for adjusting the position of the patient table, a motor control system, adapted to process control instructions for the patient table and arrange the provision of power to the at least one motor, a standby power source, a mains power input delivering mains electrical power to the motor control system and to the standby power source, a standby control system, adapted to process control instructions from the control panel and arrange the provision of power to the at least one motor from the standby power source.

The standby power source can includes a lead-acid accumulator (battery), and/or capacitive energy store.

A suitable switch can be provided, to connect the at least one motor to either the motor control system or the standby control system. This is preferably under the control of the standby control system, and/or can default to connecting the at least one motor to the standby control system.

The motor control system will usually be adapted to process control instructions from both the control panel and an external source of control instructions for the patient table. In this respect, it differs from the standby control system that the invention proposes be provided in addition, as it is envisaged that the latter only react to instructions from the control panel. However, the standby control system could accept instructions from elsewhere if that were consistent with the other aims of the invention.

The standby control system can be integrated into the standby power source, or the control panel.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
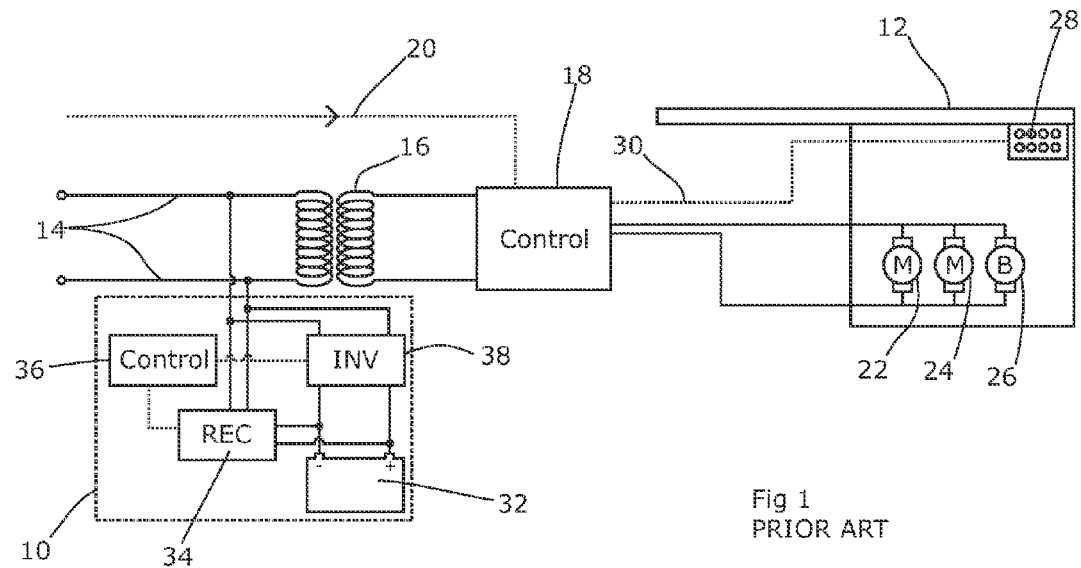
FIG. 1 shows a known arrangement for a uninterruptible power supply (UPS) supporting a patient table.

Referring to FIG. 1, the typical arrangement of a known UPS-based backup 10 for a patient table 12 is shown in a schematic form. Electrical supplies are shown as solid lines, and data connections are shown as dotted lines. Thus, an incoming 240 volt AC mains power supply 14 leads to a transformer 16 which provides 24 volt AC power to a control system 18. This receives data 20 from a treatment controller (or is an integral part of that controller) and sends power out to drive motors 22, 24 illustrated schematically within the patient table 12 and to a brake mechanism 26 for the table. The table 12 also has a manual control panel 28 which allows an operator to take manual control of the table and raise and lower it, for example to help a patient onto or off the table. A data connection 30 conveys these instructions to the control unit 18. Thus, the control unit 18 accepts control instructions for the patient table from both an external source and from the manual control panel 28, decides which has precedence, and actuates the table motors as necessary.

If the power supply 14 were to fail, this entire system would become inoperative. The operator would then be unable to lower (or otherwise adjust) the table manually so as to allow a patient off the table. If this happened during a treatment, then it would be problematic. As a result, it is usual to fit an uninterruptible power supply (UPS) 10 as shown by the dashed lines. This contains a substantial battery 32, usually lead-acid, which is charged by a rectifier circuit 34 powered by the 240V mains AC supply 14. A control circuit 36 monitors the mains AC voltage and controls the rectifier 34 to keep the battery 32 fully charged. When a failure of the mains power 14 is detected by the control circuit 36, it activates an inverter circuit 38. This is powered by the battery 32 and provides a 240V AC output which the UPS 10 provides to the transformer 16. In this way, continued operation of the patient support is possible, for as long as the battery 32 lasts.

The capacity of the battery is therefore critical. This must be enough to power the inverter 38, the transformer 16, and the control system 18 for long enough to allow the operators to react to and deal with the power failure, and to also power the motors 22, 24 and brake 26 during the process of assisting the patient off the table 12, all with a suitable safety margin. All batteries, including lead-acid batteries, start to lose capacity over time if subjected to repeated charge/discharge cycles, and such cycles are inherent to the operation of a UPS to some degree during normal operation. Therefore, over time the capacity of the battery 32 will slowly decline and eventually it will need to be replaced.

Other forms of energy storage such as capacitors do not decline in capacity over time in this way. However, they do not have sufficient capacity at a reasonable cost to make them viable for use in this context. Although some modern "supercapacitors" and "ultracapacitors" have almost enough capacity, their cost is prohibitive and regular replacement of lead-acid batteries is the better choice.

Figure 2:
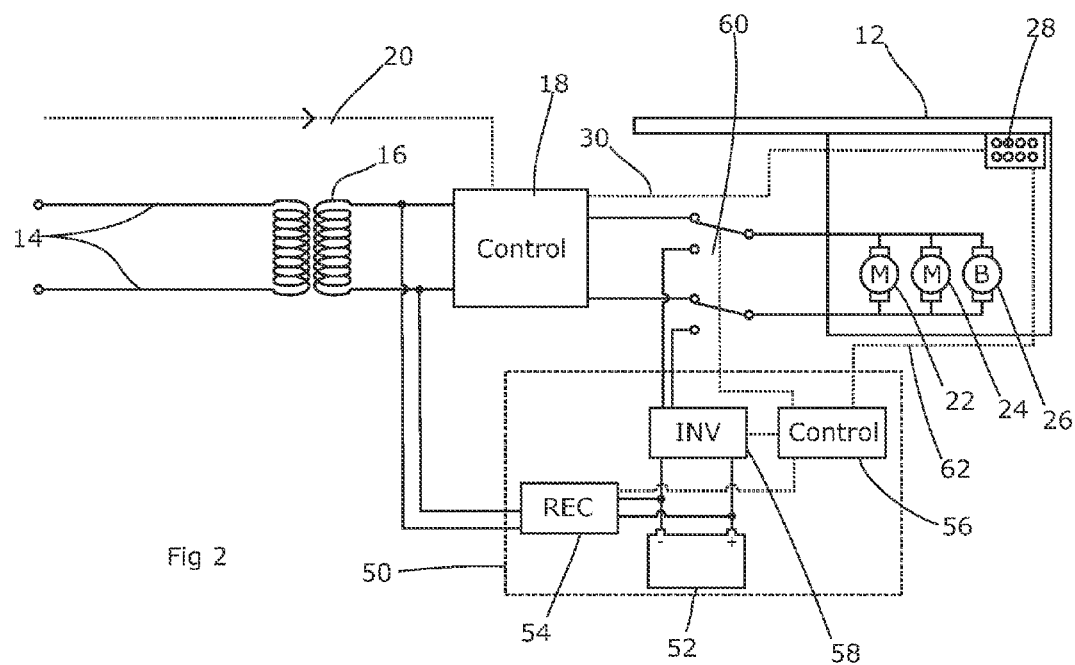
FIG. 2 shows an arrangement according to the present invention.

FIG. 2 illustrates the system according to the present invention, using like reference numerals to denote like parts. The mains AC power supply 14, the transformer 16, and the control system 18 remain the same, as do the patient support 12 and the manual control panel 28. However, the UPS 10 of FIG. 1 (which may be a standard off-the-shelf item) is replaced with a dedicated UPS 50. This includes a battery or other energy store 52, which is kept charged by a rectifier 54 that receives power from the mains supply 14, either directly or indirectly via the transformer 16 (as shown) or from other powered parts of the system such as the control unit 18. A UPS controller 56 controls this process and, as a result, can note the quality of the power supply to the rectifier 54. If this fails, then the UPS control 56 arranges for the necessary output voltage of 24V (or whatever supply voltage is needed by the motors 22, 24 & brake 26) to be fed directly to the motors (etc) via a switch 60, controlled by the UPS controller 56. An inverter 58 is shown, which will only be required for AC-driven motors. The use of DC motors will allow the inverter 58 to be omitted.

A data link 62 is provided from the manual control panel 28 to the UPS controller 56, so that the UPS controller 56 can see what commands are being made of the table by the operator and provide power to the motors 22, 24 and brake 26 as required. This can be configured as required, either by allowing the controller 56 to "sniff" data passing between the manual control panel 28 and the control unit 18 or by simply duplicating the output of the pushbutton (etc) switches of the manual control panel 28 to the UPS control unit 56.

The switch 60 is a double-throw switch with sufficient poles to connect all of the motors 22, 24 and brake(s) 26 to the inverter 58 instead of the control unit 18. It can be an electromechanical switch, or one or more solid-state devices, as desired. It should preferably default to routing power to the motors (etc) from the inverter 58 in the absence of external power, for obvious reasons.

The definition of failure for the mains power supply 14 and/or the transformer 16 can be as desired, usually either a complete loss of power (zero volts) or power less than a predetermined minimum (such as 50V or 100V).

Figure 3:
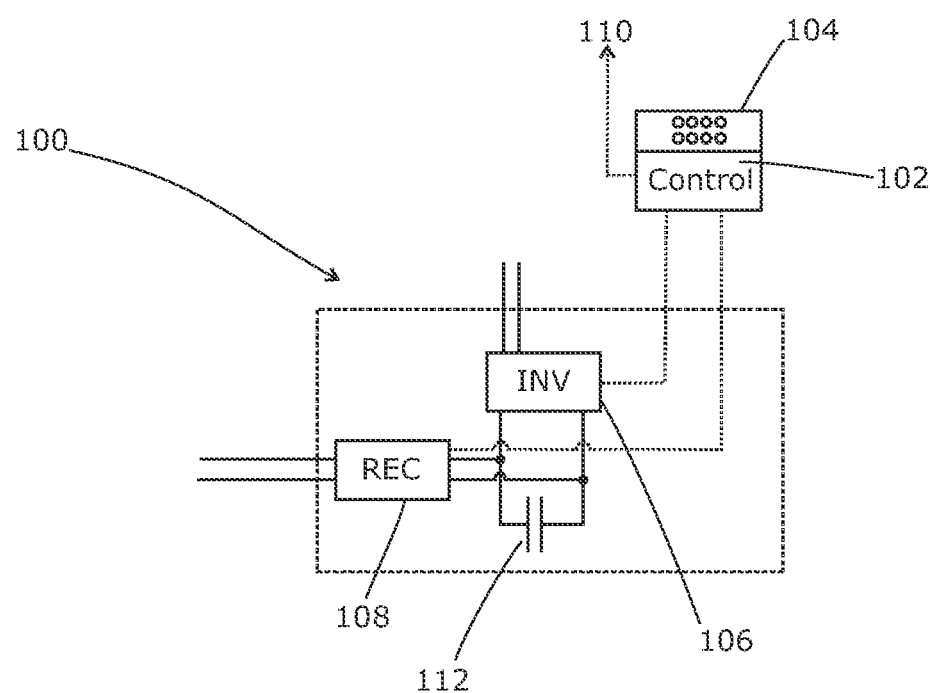
FIG. 3 shows an alternative arrangement.

FIG. 3 shows an alternative arrangement for the UPS section 100 of the apparatus. The UPS control unit 102 is integrated into the manual control panel 104, but retains connections to the inverter 106, rectifier 108 and switch 110. The battery 52 of the arrangement of FIG. 2 is also replaced with a capacitive energy store 112 in the form of a super- or ultra-capacitor. Otherwise, the arrangement of FIG. 3 is the same as FIG. 2. It should be noted that either or both of these changes can be made independently.

As a result of the above arrangements, during a power outage the battery 52 needs only support the inverter, 58, UPS control 56 and the motors 22, 24 and brake(s) 26. The full control unit 18 and the losses in the transformer 16 need not be catered for. As the UPS control unit 56 has significantly narrower remit than the full control unit 18, its power demands can be minimised. This means that the necessary capacity of the battery 52 is significantly reduced.

This reduction in necessary capacity can be deployed in a number of ways. A smaller capacity lead-acid unit could be provided, with a consequential lower initial cost and lower replacement cost. Alternatively, a large-capacity lead-acid unit could be provided, as before, but the maintenance period before replacement was necessary could be extended as the available capacity from the unit could be allowed to drop further. In a further alternative, the reduced capacity required means that a capacitive energy store such as a supercapacitor or ultracapacitor could be provided at a reasonable initial cost instead of the battery 52, thereby substantially eliminating the need for scheduled replacement.

It will of course be understood that many variations may be made to the above-described embodiment without departing from the scope of the present invention.

The invention claimed is:

1. A patient support, comprising:
   a patient table provided with a control panel;
   at least one electrically-powered motor for adjusting the position of the patient table;
   a motor control system, adapted to process control instructions for the patient table and arrange the provision of power to the at least one motor;
   a standby power source;
   a mains power input delivering mains electrical power to the motor control system and to the standby power source;
   a standby control system, adapted to process control instructions from the control panel and arrange the provision of power to the at least one motor from the standby power source.

2. A patient support according to claim 1 in which the standby power source includes a capacitive energy store.

3. A patient support according to claim 1 further comprising a switch adapted to connect the at least one motor to either the motor control system or the standby control system.

4. A patient support according to claim 3 in which the switch is under the control of the standby control system.

5. A patient support according to claim 3 in which the switch defaults to connecting the at least one motor to the standby control system.

6. A patient support according to any of claims 1-5 in which the motor control system is adapted to process control instructions from both the control panel and an external source of control instructions for the patient table.

7. A patient support according to any of claims 1-5 in which the standby control system is integrated into the standby power source.

8. A patient support according to any of claims 1-5 in which the standby control system is integrated into the control panel.

* * * * *